United States Patent
Raab

[11] Patent Number: 6,136,038
[45] Date of Patent: Oct. 24, 2000

[54] BONE CONNECTIVE PROSTHESIS AND METHOD OF FORMING SAME

[75] Inventor: Simon Raab, Longwood, Fla.

[73] Assignee: Xenon Research, Inc., Lake Mary, Fla.

[21] Appl. No.: 08/999,414

[22] Filed: Dec. 29, 1997

Related U.S. Application Data

[60] Provisional application No. 60/034,385, Dec. 30, 1996.

[51] Int. Cl.[7] .............................. A61F 2/30; A61L 27/28; A61L 24/00
[52] U.S. Cl. ...................... 623/23.37; 523/116; 623/901; 606/76
[58] Field of Search .................................. 623/11, 16, 18; 606/76; 523/105, 113, 116, 117

[56] References Cited

U.S. PATENT DOCUMENTS

| | | |
|---|---|---|
| 3,446,875 | 5/1969 | Brückmann et al. |
| 4,268,639 | 5/1981 | Seidel et al. |
| 4,336,618 | 6/1982 | Raab . |
| 4,341,691 | 7/1982 | Anuta . |
| 4,404,327 | 9/1983 | Crugnola et al. |
| 4,536,158 | 8/1985 | Bruins et al. |
| 4,645,456 | 2/1987 | James . |
| 4,648,845 | 3/1987 | Orlowski et al. |
| 4,718,910 | 1/1988 | Draenert . |
| 4,719,149 | 1/1988 | Aasen et al. |
| 4,837,279 | 6/1989 | Arroyo . |
| 4,880,660 | 11/1989 | Aasen et al. |
| 4,937,144 | 6/1990 | Podszun et al. |
| 5,147,903 | 9/1992 | Podszun et al. |
| 5,258,420 | 11/1993 | Posey-Dowty et al. |
| 5,264,513 | 11/1993 | Ikemura et al. |
| 5,525,648 | 6/1996 | Aasen et al. |
| 5,534,562 | 7/1996 | Jensen et al. |

FOREIGN PATENT DOCUMENTS

WO 88/03811   6/1988   WIPO .

*Primary Examiner*—Mickey Yu
*Assistant Examiner*—Choon P. Koh
*Attorney, Agent, or Firm*—Cantor Colburn LLP

[57] ABSTRACT

A bone connective prosthesis and method of forming same comprising the addition of a biocompatible plasticizer to a PMMA film and/or bone cement, which preferably copolymerizes with the PMMA film and/or bone cement. Preferably, this plasticizer comprises the FDA approved, biocompatible hydrophilic monomer known as 2-hydroxyethyl methacrylate (commonly referred to as "HEMA") and its associated water. HEMA has the ability to absorb water. An important feature of this invention is that this ability to absorb water results in a measurable and controllable plasticization.

In one embodiment of the present invention, the plasticizer (HEMA and its associated water) copolymerizes with the PMMA film to form a PMMA/HEMA coating which is preferably used as a coating on a bone prosthesis. In a further embodiment, the plasticizer (HEMA and its associated water) copolymerizes with a PMMA base bone cement to form a PMMA/HEMA bone cement. In accordance with the present invention, one side of a PMMA/HEMA copolymer film is disposed on at least a portion of the surface of a prosthetic element. The other side of the copolymer film forms a bonding surface, wherein the bonding surface is adapted to be fixedly attached to a bone by a bone cement. Preferably, a PMMA/HEMA copolymer bone cement is used to fixedly adhere the prosthesis to the bone. The weight ratio of PMMA and HEMA in the copolymer bonding film or bone cement is not critical; however, the portion of HEMA should suitably be in the range between 2 weight % and 99 weight %.

47 Claims, 2 Drawing Sheets

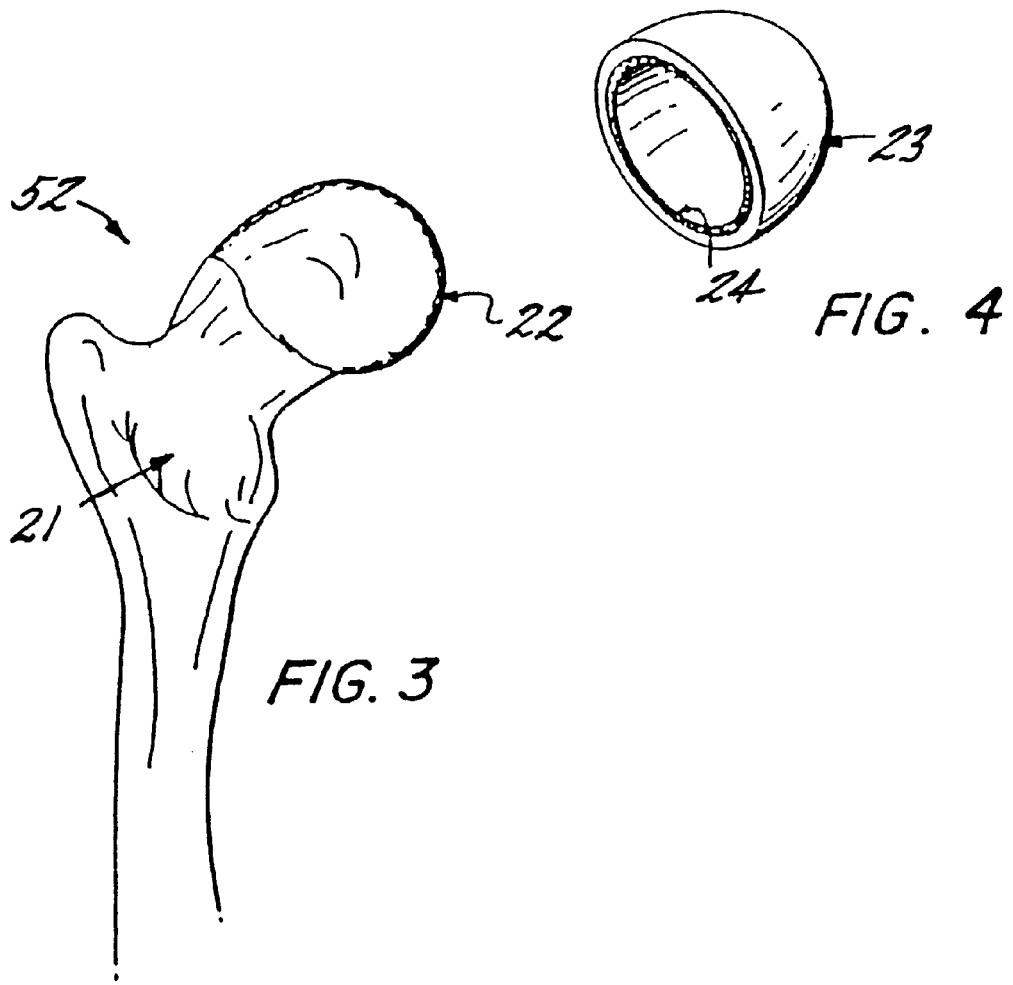
FIG. 3
FIG. 4
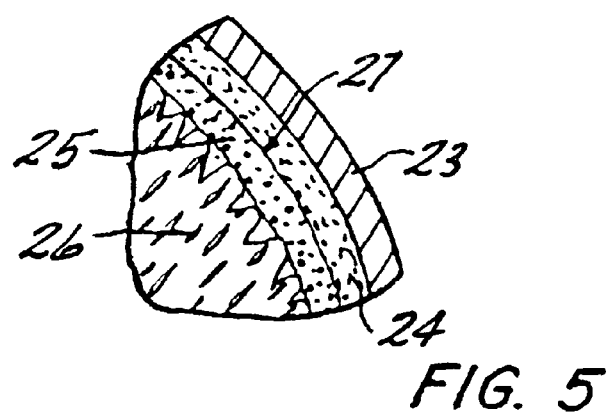
FIG. 5

BONE CONNECTIVE PROSTHESIS AND METHOD OF FORMING SAME

CROSS REFERENCE TO RELATED APPLICATION

This application claims the benefit of U.S. Provisional Application No. 60/034,385 filed Dec. 30, 1996.

BACKGROUND OF THE INVENTION

1. Field of the Invention

The present invention relates to a prothesis adapted to be fixedly attached to bone by a cement. More particularly, the present invention is directed towards a prothesis adapted to maximize the strength and durability of the prothesis/bone cement adherence.

2. Description of the Prior Art

In the field of orthopedic surgery, ZIMALOY manufactured by Zimmer, U.S.A. Inc., a chromium-cobalt-molybdenum alloy, stainless steel, titanium alloys, and polymerized materials such as ultra high molecular weight polyethylene (hereinafter UHMWPE) have been used successfully to replace the ends of long bones and joints, including the hip joint. However, there exists a severe limitation with respect to such orthopedic surgery, namely, coupling of the prosthesis to bone. Due to such factors as mechanical stress, fatigue, corrosion, etc., the prosthesis/bone cement joints have been prone to failure.

Present methods of utilizing such bone prosthesis involve the use of a prosthesis having a stem portion which is inserted into the interior of a bone. A bone cement comprising a mixture of polymethylmethacrylate (hereinafter PMMA) polymer and methyl methacrylate monomer and optionally including a styrene copolymer of PMMA is likewise inserted into the bone cavity and utilized to couple the stem of the implant to the bone itself. Experience has demonstrated, however, that serious drawbacks exist with respect to the coupling between the prosthesis stem and the bone cement. Attempted solutions to this problem have been directed primarily toward strengthening the prosthesis/bone cement interface by means of gross mechanical interlock involving, for example, dove tails, small stems, and the like. Such devices result in stress concentrations that can exceed the strength of the bone cement as well as cause non-physiological force distribution in the bone.

Adherence at the interface between the implant and PMMA is greatly restricted by current industrial and surgical practices. For instance, the PMMA cement is typically applied in a highly viscous, doughy state with the result that the degree of contact between the implant and the cement is inadequate. Moreover, the existence of wear boundary layers such as contaminants and weak metal oxides on the surface of the implant have also caused problems. Weak boundary layers may be due to the composition of the implant or to the process of forming the same. Thus, in the case of a metal implant, the surface of the implant normally includes weak metal oxides as weak boundary layers. In the case of a polymeric implant, the surface of the implant normally includes a weak boundary layer comprising monomer, partially polymerized or low molecular weight polymer and contaminants comprising mold release agents, and the like. Finally, the implant may come in contact with air, blood or water prior to being inserted into the bone, thereby becoming contaminated. The existence of weak boundary layers, e.g., surface contaminants, is detrimental to the formation of good implant bone cement adherence. Thus, the strength of such joints has been dependent upon gross mechanical interlock. Such difficulties in the formation of a satisfactory prosthesis/bone cement connection have also caused the result that mere resurfacing of a deteriorated joint, e.g., a deteriorated hip joint due to arthritis, was not readily accomplished. Thus, in the case of a deteriorated articular surface, e.g., surface of the head or ball in a ball and socket joint, the entire head of the bone is generally removed and prosthetic head connected to the bone, although in some instances, resurfacing implants have been used with bone cement.

U.S. Pat. No. 4,336,618 to Simon Raab which is assigned to the assignee hereof, all of the contents of which are incorporated herein by reference, taught that the aforementioned prosthesis fixation problems could be overcome by treating at least that portion of the prosthesis which is adapted to be connected to bone in order to provide a PMMA film fixedly adhered to said portions of the prosthesis. Prior to the application of the PMMA film, the surface to be coated is treated to prevent formation of a weak boundary layer upon bonding of a bone cement to an applied film. Thereafter, a PMMA film is applied by dipping, painting, spraying, etc., and finally, after the film has dried, it is annealed to remove any stresses in the film.

The resultant prosthesis has a film of PMMA firmly adhered to the surface thereof. This PMMA film adhesively interacts molecularly with PMMA bone cement. Accordingly, the adherence of a prosthesis adhesively connected to bone by means of a PMMA cement can be drastically increased.

To summarize the teaching of U.S. Pat. No. 4,336,618 discussed hereinabove, the methods used for the application of the precoats typically include the preparation of the metal surface by cleaning and passivation, and then either solvent based lacquer polymerizing solutions of monomer catalyst, or inhibitor and polymer electrostatically-applied or dip-applied power coatings. In all cases, some curing and/or annealing heat cycles are used. The overall composition of the coating have been limited to PMMA and other standard approved inhibitors and catalysts.

Although the U.S. Pat. No. 4,336,618 is a great improvement over the previous prior art, the literature or implant fixation failure has focussed on the interface and bulk material strength measured typically in low strain/load rate tests. The strain and/or load rates can affect the nature of plastic failure modes. This can be best understood when one observes the fact that water becomes a very hard surface as in the example of a water skier landing in the water at a high speed. This impact in the water at high speed causes the water surface to become very hard. This same principle applies to plastics which are viscoelastic materials. The properties of viscoelastic materials change with the load application rate and the related strain or deformation rate.

Impact is defined as the application of a load over a short period of time such as $1/100$th to 1 second. A plastic sample subjected to an applied load of 100 pounds will respond very differently if the period of time is ten seconds as compared to a period of time of one second. Plastics under impact load will deform far less before failure than under low rate loading. Additionally, plastic failure usually starts after elongation is finished and is generally due to fracture initiated at a flaw. The lack of strain or elongation during impact means that the fracture point is quickly reached and the material fails at a far smaller strain level than usual and/or is less able to absorb impact energy.

In lieu of the above and despite the large improvement in the prior art as taught by the U.S. Pat. No. 4,336,618, there appears to be a need for an improved bone connective prosthesis and method of forming the same to lower implant fixation failure rates and particularly those failures that are a result of impact and shock conditions.

SUMMARY OF THE INVENTION

The above-discussed and other problems and deficiencies of the prior art are overcome or alleviated by the improved bone connective prosthesis and method of forming same of the present invention, comprising the addition of a biocompatible plasticizer to the PMMA film and/or cement, which preferably copolymerizes with the PMMA film and/or cement. Preferably, this plasticizer comprises the FDA approved, biocompatible hydrophilic monomer known as 2-hydroxyethyl methacrylate (commonly referred to as "HEMA") and its associated water. HEMA has the ability to absorb water. An important feature of this invention is that this ability to absorb water results in a measurable and controllable plasticization. Without being bound by theory, it is believed that the water hydration characteristic of HEMA advantageously results in the controllable plasticization of the material. Hydration can occur in a variety of ways. For example, the PMMA/HEMA copolymer may be applied to the prosthetic element by a dry coat form thus forming a dry coated prosthesis that may be packaged as such. The prosthesis and in particular the copolymer film may then be prehydrated by packaging the prosthesis in a saline solution or in other suitable solutions whereby the PMMA/HEMA copolymer is hydrated. The prosthesis and copolymer film may be hydrated directly by the physician by placing the prosthesis in a saline solution for a time period sufficient for hydration to occur resulting in plasticization of the material. It is also within the scope of this invention, that the coated prosthesis may be hydrated by placing the prosthesis into a body where natural fluids hydrate the copolymer and water bonds to the HEMA and the coating. HEMA copolymerizes with PMMA and therefore will not leach out of the PMMA and thus produces an effective copolymer for use, preferably, as a bonding film on a prosthetic element.

In one embodiment of the present invention, the plasticizer (HEMA and its associated water) copolymerizes with the PMMA film to form a PMMA/HEMA coating which is preferably used as a coating on a bone prosthesis. In a further embodiment, the plasticizer (HEMA and its associated water) copolymerizes with a PMMA base bone cement to form a PMMA/HEMA bone cement. Preferably, the bone cement comprises a PMMA/HEMA copolymer base in a powdery copolymer component in the form, for example, of spheres or granules. Further copolymerization of the bone cement can occur with the addition of polymerization initiators known in the art and by the addition of monomer to material. Preferably, a PMMA/HEMA copolymer film is fixedly adhered to at least a portion of the surface of a prosthetic element and a PMMA/HEMA copolymer bone cement is used to fixedly adhere the coated prosthetic element to a bone. The weight ratio of PMMA and HEMA in the copolmyer bonding film or bone cement is not critical; however, the portion of HEMA should suitably be in the range between 2 weight % and 99 weight %. Preferably, the HEMA is present in an amount effective to provide enhanced bonding and plasticization without adversely affecting the strength and other characteristics of the copolymer film and/or bone cement.

The above-discussed and other features and advantages of the present invention will be appreciated and understood by those of ordinary skill in the art from the following detailed discussion and drawings.

BRIEF DESCRIPTION OF THE DRAWINGS

Referring now to the drawings, wherein like elements are numbered alike in the several FIGURES:

FIG. 3 is a side elevational view of a human femur having a deteriorated head surface;

FIG. 4 is a perspective view of a prosthesis having a PMMA/HEMA coating on the bone connective surface thereof wherein the prosthesis may be utilized for resurfacing a deteriorated head surface of a ball and socket joint thus obviating the need for removal of the head portion of the joint; and FIG. 5 is an enlarged fragmentary cross-section of a deteriorated femur head bearing the resurfacing prosthesis of FIG. 4.

DETAILED DESCRIPTION OF THE PREFERRED EMBODIMENT

Just as microscopic flaws such as crazing and trapped air bubbles are stress concentrators and are often the focus for failure, dissimilar materials may also cause stress concentrations due to differences in strain under load. In implant fixation, this situation is found at the metal-plastic interface. The ability of the interface to dissipate the stress due to these strain differences is also influenced by the strain behavior of the plastic.

It is known that the impact resistance of plastics may be enhanced by the addition of plasticizers. PMMA is known as and is considered to be a glassy, rather brittle polymer and is highly prone to "brittle plastic failure". Plasticization can be achieved in various ways and usually is accomplished by the addition of plasticizers of various kinds to affect impact strength. Impact strength may also be improved by simply changing the yield with reinforcing additives such as fibers. Also, crack growth inhibitors such as particulate fillers may be used to increase impact resistance by stopping catastrophic fracture propagation.

In the typical implant fixation as disclosed, in for example, U.S. Pat. No. 4,336,618, the implant fixation is typically inserted into a PMMA bone cement in proximity to bone. The cement and interfaces are normally highly flawed with the resulting interfaces being the weakest link in the fixation. In accordance with U.S. Pat. No. 4,336,618, the cement interface is enhanced with low viscosity cement and pressure injected into the porous bone, thus creating a mechanical interlock.

However, the loads or forces existing at the implant area of a typical implant such as, for example, a typical hip joint implant may exceed by several times the weight of the body, due to the lever mechanics and the inertia shock of natural abrupt motions. For instance, in individual's body, when falling from an upright position, can be likened to the swing of a hammer head onto the head of a nail. Rest the hammer on the nail head and the nail will not move appreciably. However, swing the hammer and when it comes to rest on the nail head, the nail will pierce the wood into which the nail is being driven because the forces imparted to the nail are very much higher. Similarly, the ability of the implant fixation complex joint to deform under high rate impact loads severely affect the longevity of the fixation without failure.

Optimum plasticization of the precoat and/or cement will therefore enhance fracture resistance under high impact loading. One of the problems with finding suitable plasticizers in the field of biological implants is the very limited range of materials that are considered biocompatible and are at the same time, effective.

Figure 1:
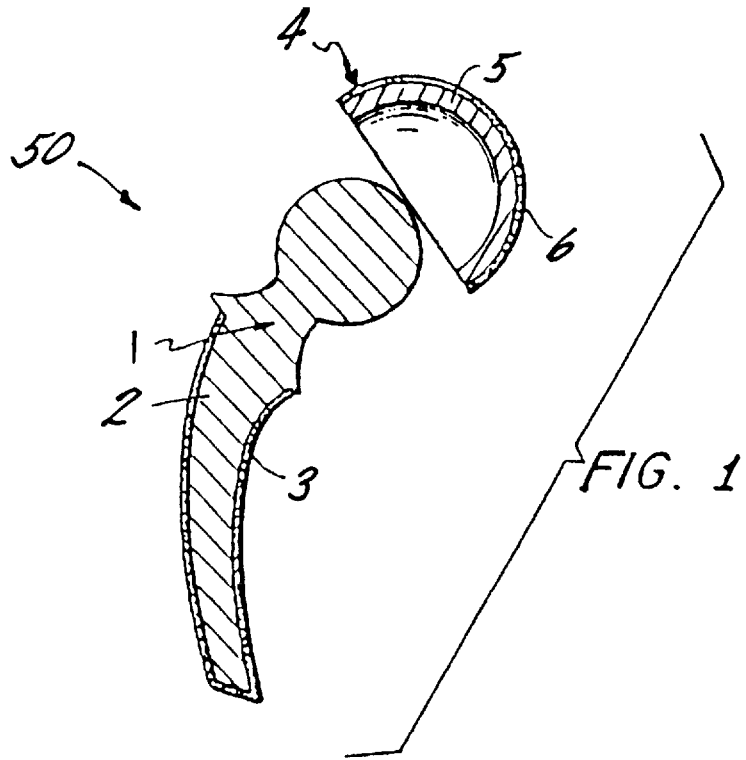
FIG. 1 is an elevational side view in longitudinal section of a PMMA and HEMA coated hip prosthesis prepared in accordance with the present invention.
Figure 2:
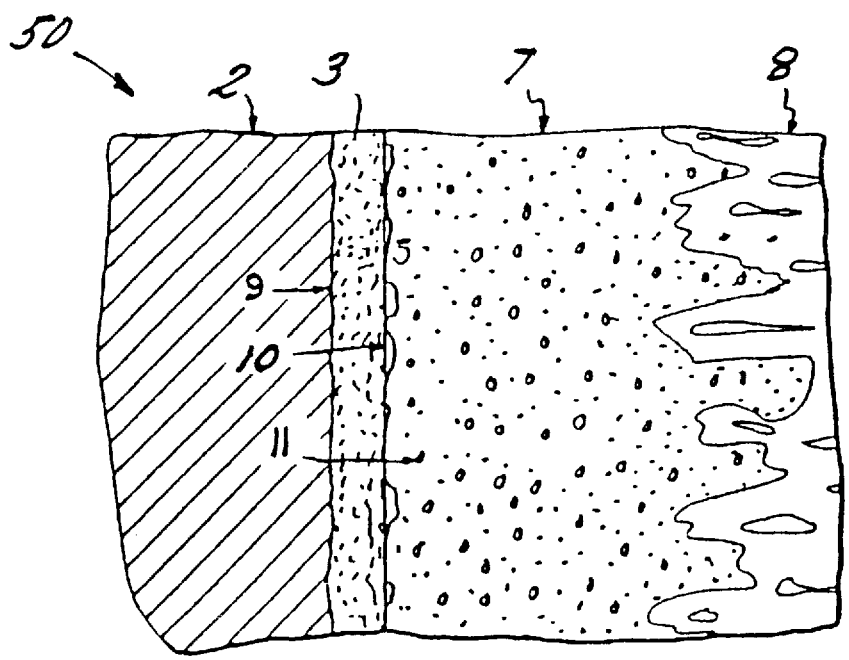
FIG. 2 is an enlarged fragmentary view of a PMMA and HEMA coated bone implant, as shown in FIG. 1, which has been fixedly adhered to the interior of a bone by means of a PMMA/HEMA bone cement.

In accordance with one embodiment of the present invention, an optimally plasticized prothesis exhibiting marked fixation improvements, along with marked resistance to fracture in the implant cement and interface areas under high impact loading, is shown by FIGS. 1 and 2 at 50. Such, prosthesis 1 comprises a prosthetic element 2 having a PMMA/HEMA copolymer film 3 fixedly adhered to at least a portion of the surface of the prosthetic element 2. HEMA is an FDA approved, biocompatible, hydrophilic co-monomer of PMMA. HEMA (2-hydroxyethyl methacrylate) is characterized by its ability to absorb water. The absorbed water results in a measurable and highly controllable plasticization. Without being bound by theory, it is believed that the water hydration characteristic of HEMA advantageously results in the controllable plasticization. Hydration can occur in a variety of ways. For example, the PMMA/HEMA copolymer may be applied to the prosthetic element by a dry coat process thus forming a dry coated prosthesis that may be packaged as such. The prosthesis and in particular the copolymer film may then be prehydrated by packaging the prosthesis in a saline solution or in other suitable solutions. The prosthesis and copolymer film may be hydrated directly by the physician by placing the prosthesis in a saline solution for a time period sufficient for hydration to occur. It is also within the scope of this invention, that the coated prosthesis may be hydrated by placing the prosthesis into a body where natural fluids hydrate the copolymer and water bonds to the HEMA and the coating. Because HEMA copolymerizes with PMMA, HEMA does not leach out of the implant joint. Also shown is a resurfacing prosthesis 4 for the socket portion of a ball and socket joint, comprising a rigid prosthetic element 5 and a PMMA/HEMA film 6.

In order to prepare a high strength PMMA/HEMA copolymer film in accordance with the present invention, the prosthetic element is first prepared. Preparation involves removal of any contaminants which may act as weak boundary layers so that the coating may be joined directly to the prosthetic element with no intervening material. In the case of a metal prosthetic element, the weak boundary layer may comprise contaminants such as dirts and oils, and additionally typically includes weak metal oxides. In the case of a polymeric prosthetic element, the weak boundary layer typically comprises contaminants such as unreacted monomer, anti-oxidation agents, and mold release agents, as well as low molecular weight polymer.

In the case of a metal prosthetic element, the treatment to prevent the formation of a weak boundary layer upon bonding of the bone cement to an applied layer comprises degreasing followed by removal of the weak metal oxides by an acid treating step, which may be followed by a desmutting and passivation step. However, any treatment which functions effectively to remove contaminants and weak metal oxides may be utilized.

The degreasing treatment may be carried out through the utilization of an aqueous alkaline solution, such as, for example, an aqueous solution of sodium hydroxide. Thus, the prosthetic element to be degreased may be immersed in a 1 N solution of sodium hydroxide which has been heated to its boiling point for 30 minutes to remove contaminants and grease. Another degreasing treatment which may be utilized with less contaminated elements comprises exposing the prosthetic element to trichloroethylene vapor. In order to determine whether or not degreasing is complete, the water break test may be utilized according to which the degreased prosthetic element is rinsed in distilled water. When the element is removed from the water, if the water beads up and runs off in less than 30 seconds, the surface is not clean enough. There should be no break in the film of water nor any tendency of the film to crawl or pucker.

Subsequent to the degreasing treatment, the metallic prosthetic element is preferably treated by acid etching in order to remove weakly bound metal oxides. Such treatment may comprise immersing the element in a sulfuric acid/water admixture at an elevated temperature of, for example, 60° C. for a period of approximately 30 minutes. Other treatments which may be used include immersing the prosthetic element in a sulfuric acid/sodium dichromate aqueous solution or treatment with other acid solutions.

It is preferred that acid etching occurring be discontinued prior to any gross surface changes occurring. Thus, it is preferred that the surface which is designed to be attached to the bone be smooth. This results in a more continuous stress concentration about the prosthetic element/bone cement interface. However, where it is desired to use an implant having a rough surface, thus promoting a greater degree of mechanical interlock, the coating of the present invention may be utilized and a stronger joint will result.

In the case of an alloy prosthetic element which has been acid etched with the sulfuric acid solution discussed above, completion of the etching reaction is evidenced by the surface of the element turning black, this is due to the presence of carbon which is a component of metal alloys. Such presence of carbon indicates that the surface has been sufficiently etched. If no carbon appears, then the etching is not complete. In order to avoid any gross surface changes, the element should be removed from the etching solution within ten seconds of the appearance of carbon. The etched element may be checked by means of a Hobsyn Tally Surface Profile or an SEM to insure that no gross surface changes have occurred.

Thereafter, any carbon remaining on the surface of the element is removed by means of a desmutting and passivation treatment. Such desmutting and passivation treatment may be carried out by means of a hydrofluoric acid/nitric acid aqueous admixture heated to an elevated temperature of approximately 60° C. Other strong oxidation reagents may be utilized if desired. When the etched element is immersed in such a solution, there should be a reaction within seconds as evidenced by a burst of bubbles as carbon is removed. This is followed by another sudden burst of bubbles evidencing a secondary reaction. At this point, the element should be removed from the desmutting and passivation solution. This treatment functions not only to remove carbon but additionally promotes the formation of a well adhered, uniform, high strength oxide surface, and is a preferred treatment step.

This initial removal of weak boundary layers may be carried out not only by chemical means, i.e. degreasing and acid etching, but also by mechanical means if desired. Thus, the prosthetic element may be treated by blasting with alumina grit to provide a virgin metal surface. Other mechanical treatments such as grinding, honing, machining, etc., may also be utilized.

Following mechanical treatment of the prosthetic element, the treated surface is immediately immersed in a passivation solution comprising, e.g. nitric and hydrofluoric acid, as above. It is preferred that the passivation treatment be carried out within a short time from the mechanical treatment. The lapse of time between mechanical treatment and passivation should be less than one minute.

Thereafter, the treated element should be rinsed in water until the water has a neutral pH. The treated element should thereafter be dried by any suitable means such as by heating in an oven or by blowing the surface dry with a warm air stream.

Once the element has dried, it is allowed to cool to room temperature prior to application of the PMMA/HEMA film thereto. Care must be taken that the clean surface not be contaminated during drying or cooling. Coupling agents such as siloxane derivatives may be applied before the coating.

Thereafter the PMMA/HEMA film is applied to the prosthetic element. The film may be applied by painting, spraying, dipping, powder coating, electrostatic coating, or in any suitable manner in the form of a lacquer, powder or emulsion. The method and form utilized will depend on a number of various factors including the desired coating thickness, strength, implant geometry and surface roughness.

The film comprises a PMMA/HEMA copolymer. It is within the scope of this invention, that other materials known in the art may be included in the film such as crosslinking agents, free radical catalysts, activators, other plasticizers, chain transfer agents, and inhibitors, as well as adhesion promoters in the form of co-polymers, such as of acrylic acid and other freely orienting polar molecules.

The plasticizer, preferably HEMA and its associated water, copolymerizes with PMMA and therefore will not leach out of the PMMA. The result is a copolymer of PMMA/HEMA which is especially suitable to be fixedly adhered to at least a portion of the surface of the prosthetic element, e.g. the bonding surface of the element to a bone. The copolymer film has a first and a second side, the first side is disposed on at least a portion of the surface of the prosthetic element, the second side forming a bonding surface being adapted to be fixedly attached to a bone by a bone cement. The weight ratio of PMMA and HEMA in the copolmyer bonding film is not critical; however, the portion of HEMA should suitably be in the range between 2 weight % and 99 weight %. Preferably, the HEMA is present in an amount effective to provide enhanced adhesion and plasticization without adversely affecting the strength and other advantageous properties of the copolymer film.

In one embodiment, the copolymer film is applied as a dry coat to the prosthetic element. The dry coat comprises a copolymer of polymethylmethacrylate 2 hydroxyethyl methacrylate and is in the form of a film. The dry coat and in particular the HEMA component may be hydrated in a variety of ways, as previously mentioned herein, in order to effectively plasticize the material.

One preferred method of applying the film to the prosthetic element comprises the application of a PMMA/HEMA lacquer to the element. Application may take the form of dipping, spraying, and the like. A PMMA/HEMA lacquer is prepared by dissolving PMMA/HEMA copolymer high molecular weight beads in a solvent such as dichloromethane. A small amount of barium sulfate may be added to the lacquer in order to keep the coated surface from crazing as well as making the coating radiopaque. The concentration of polymer in the solution should be in the range of 0.01 g. per ml. to about 0.8 g. per ml., preferably from about 0.2 g. per ml. to about 0.4 g. per ml., most preferably from about 0.25 g. per ml. to about 0.35 g. per ml.

The prosthetic element is immersed in the lacquer for a period of time sufficient to form a suitable coating on the surface of the element. Such a period of time may range from about 5 seconds to about 60 minutes, preferably from about 15 minutes to about 60 minutes, most preferably from about 25 to about 35 minutes.

Another method for applying the film to the prosthetic element comprises the application of PMMA/HEMA to the prosthetic element, the PMMA/HEMA film should be annealed by exposing the coated element to a temperature above that of the glass transition temperature of PMMA/HEMA, i.e. 70°–90° C., preferably 80° C. The curing or annealing treatment is necessary to insure complete co-polymerization and removal of any volatile components from the film. High pressures, i.e. greater than 100 psi may be applied to inhibit bubble formation. Moreover, by heating the film to a temperature above the glass transition temperature of PMMA/HEMA, any mechanical stresses in the film developed during the drying thereof will be eliminated.

The rate at which the coated element is cooled following the annealing treatment is preferably carefully controlled to insure that it preferably does not exceed about 1.5° C. per minute until the coated element reaches a temperature of about 80° C. This insures that only minimal stresses are formed in the film during cooling. If desired the film may be crosslinked by chemical and/or radiation techniques.

The thickness of the film thus produced is not of critical importance; however, the preferred minimum thickness of the film should be about 0.0001 inch, more preferably about 0.001 inch, most preferably about 0.002 inch. In contrast to PMMA films, the PMMA/HEMA copolymer films as described herein have an effective percent elongation. Such elongation provides enhanced ability to absorb a shock stress from external sources, thereby reducing the likelihood of fracture of the interface from such stress.

Upon completion of the annealing or curing of the PMMA/HEMA film, the coated prosthetic element is ready for use as a prosthesis. If the prosthesis is a bone implant prosthesis, the interior of the bone is removed and cleaned and a PMMA or PMMA/HEMA bone cement is applied to the interior of the bone. Thereafter, the implant portion of the prosthesis, coated in accordance with the present invention is inserted into the interior of the bone. If desired, the coating may be softened with a solvent such as MMA monomer prior to insertion into the bone. This causes the PMMA/HEMA to swell and soften, thus allowing for greater mechanical and chemical interaction between the coating and the bone cement.

The bone cement of the present invention may be used to fixedly attach a prosthesis to a bone so that a strong bonding interface results between the prosthesis and the bone. In accordance with the present invention, a prosthetic element having a PMMA/HEMA copolymer film is also fixedly attached to a bone with the bone cement of the present invention. The prosthetic element is anchored (attached) to a bone by means of a plastic mass which is known as the bone cement. Known bone cements are cold polymerizing two-component based plastics consisting of a monomer and a powdery polymer component in the form of granuals or spheres. Conventional bone cements are prepared with a PMMA base. The bone cement is prepared according to methods known in the art, for example by a mixing system. The weight ratio of PMMA and HEMA in the bone cement is not critical; however, the portion of HEMA should suitably be in the range between 2 weight % and 99 weight %. Preferably, the HEMA is present in an amount to provide enhanced bonding and plasticization without adversely affecting the strength and other advantageous properties of the bone cement.

Using a bone cement having a PMMA/HEMA base to bond a prosthetic element coated with a PMMA/HEMA copolymer film results in a strong bonding interface between the PMMA/HEMA copolymer film and the bone. The interface is shown to be free of defects and any weak boundary layer upon the bonding of the prosthesis to the bone by the bone cement.

In FIG. 1, PMMA/HEMA copolymer film 3 is adhesively fixed to copolymer PMMA/HEMA film 6 when prosthesis 1 is connected to resurfacing prosthesis 4.

In accordance with another embodiment of the present invention, a PMMA/HEMA copolymer bone cement is used to fixedly adhere a coated prosthesis to a bone. HEMA is a biocompatible plasticizer which copolymerizes with PMMA and therefore produces a PMMA/HEMA copolymer bone cement in which the HEMA will not leach out of the PMMA. The use of HEMA in the bone cement results in improved coupling between a PMMA/HEMA coated prosthetic element. Preferably, the prosthetic element is itself also coated with a PMMA/HEMA copolymer. FIG. 2 is an enlarged fragmentary view of a coated prosthesis which has been fixedly adhered to bone by means of a PMMA/HEMA copolymer bone cement. Prosthesis element 2 is connected to bone cement 7 via the PMMA/HEMA film 3. Bone 8 is shown to be adhered to the bone cement 7. The interface 9 between the PMMA/HEMA film 3 and the prosthetic element 2 is shown to be free of defects and any weak boundary layer due to the precoating treatment of the prosthetic element 2 in accordance with this invention. The interface 11 between the PMMA/HEMA coating or film 3 and bone cement 10 shows both a strong chemical and mechanical adherence. Flaws 11 in the bone cement 10 may be displaced away from the interface 9 due to the interaction of the film 3 and bone cement 10.

When a PMMA/HEMA coating is applied to a prosthetic element in accordance with the present invention, the resulting prosthesis may be joined to bone cement and will exhibit markedly superior adherence compared to that obtained by use of an uncoated prosthesis or compared to that obtained by use of a coated prosthesis wherein the element precoating treatment where the annealing treatment is not utilized. Similarly, use of a PMMA/HEMA bone cement in accordance with the present invention exhibits markedly superior adherence between the prosthesis and bone cement.

The effect of the improved adherence between the prosthesis and bone cement results not only in improved adhesion of bone implant prosthesis to the interior of a bone but moreover may eliminate in some cases the need for using an implant stem. Thus, stems have been used in prosthesis to implant a steel object securely into the bone. However, typically, the reason for the implant is a surface deterioration of the joint, for example, due to arthritis, but a mere resurfacing was not easily accomplished because of the fixation problems. Recent advances in the application of cement to bone involves the pressurization of cement deep into the pores of bones creating intimate interlock. The only problem remaining has been the attachment of a metal surface to the cement without a stem. Such problems may be solved utilizing the PMMA/HEMA coated prostheses of the present invention.

Additionally, it should be noted that the PMMA/HEMA coated prosthesis is especially suited to prosthesis subject to shock such as the "ball" position of a human femur as compared with the prior art.

Where a prosthetic element comprising a polymer, especially UHMWPE (ultra-high molecular weight polyethylene) is to be utilized, a somewhat different weak boundary layer removal treatment is utilized. Such treatment comprises either an oxidation treatment or a treatment referred to by the acronym "casing" (crosslinking by activated species of inert gases). The oxidation treatment may be performed by corona discharge, flame treatment or an acid treatment, such as chromic acid, etc. The oxidation treatment accomplishes the removal of contaminants and low molecular weight polymers, i.e. polyethylene.

It is preferred that the polymeric element be degreased prior to the oxidation or casing treatment. Such degreasing treatment is usually readily accomplished by immersing the polymeric element in trichloroethylene liquid for several seconds.

As previously mentioned, in lieu of surface oxidation treatment, the polymeric element may be treated by "casing". This process consists of allowing electronically excited species of rare gasses to impinge upon the surface of the polymer. A these mestastable and ionic gasses come in contact with polyethylene, for example, they cause abstraction of hydrogen atoms and formation of polymer radicals at and near the surface of the polymer. The radicals formed by this process interact to form crosslinks and unsaturated groups without appreciable scission of the polymer chain. The mechanical strength of the surface region is increased remarkably by the formation of a gel matrix. Thus, a weak boundary layer is transformed into a strong boundary layer. Wettability of the surface is relatively unaffected. Contact of the activated gas with the polymer surface for a time as short as one second will remarkably improve adhesive joint strength. Longer exposure times may be necessary when utilizing a more inert polymeric element such as, for instance, polytetrafluoroethylene. It is believed that substitution of casing for the oxidation treatment results in a more well adhered PMMA/HEMA film.

Upon completion of the oxidation and/or casing treatment of the polymer surface, a PMMA/HEMA coating is applied to the polymeric element in the same manner as previously discussed with respect to the metal element. The PMMA/HEMA film should thereafter be annealed or cured as with the coated alloy element. Annealing at a temperature of about 100° C. is sufficient with a UHMWPE element.

When a PMMA/HEMA coating is applied to a prosthetic in accordance with the present invention, the resulting prosthesis may be joined to bone cement and will exhibit markedly superior adherence to the same when compared to the adherence of a coated prosthesis wherein the element precoating treatment and/or where the annealing treatment is not utilized.

The effect of the improved adherence between the prosthesis and bone cement results not only in improved adhesion of bone implant prosthesis to the interior of a bone but moreover may eliminate in some cases the need for using an implant stem. Thus, stems have been used in prosthetics to implant a steel object securely into the bone. However, typically, the reason for the implant is a surface deterioration of the joint, for example, due to arthritis, but a mere surfacing was not easily accomplished because of the fixation problems.

Turning now to FIG. 3, there is shown a human femur 21 in elevational side view, with the head 52 thereof having a deteriorated surface 22, due for example, to arthritis or other known deterioration condition. Prior art would have preferred the removal of the entire head 52 of the femur and substitution of a complete prosthetic head connected to the femur by means of a stem insertion. However, by utilizing the present invention, a new exterior surface may be fixedly attached to the deteriorated surface 22 as can be seen in FIGS. 4 and 5.

The new prosthetic element 23, which may be an alloy, and an inner surface 24 comprising PMMA/HEMA can be utilized to cover the deteriorated surface 22 in accordance with the present invention. This approach is quite similar to the approach taken in FIGS. 3, 4 and 5 of U.S. Pat. No. 4,336,618 but since the PMMA/HEMA surface 24 in accordance with the present invention has far more impact strength, it can be seen that this invention is more favorable relative to the prior art of U.S. Pat. No. 4,336,618 for such prosthetic devices as depicted in FIGS. 3, 4 and 5. Inner surface 24 (comprised of PMMA/HEMA) will strongly adhere to both the prosthetic element 23 and the damaged head 52 of the femur when prepared in accordance to the detailed process of U.S. Pat. No. 4,336,618. Of course, it is to be understood that any other prosthesis would result in superior fixation when prepared in accordance with the present invention.

FIG. 5 is an enlargement of a fragmentary cross-section of a femur head after resurfacing. Bone cement 25 is shown extending deeply into the surface of the bone 26. The bone cement 25 is connected to the PMMA/HEMA film 24 by molecular bonding at the PMMA/HEMA—PMMA/HEMA bone cement interface 27. The prosthetic element 23 is thus connected by means of the PMMA/HEMA film 24 and the bone cement 25 to the surface of bone 26. It is envisioned that resurfacing prosthesis of the present invention may be used not only for deteriorated ball and socket joints but may be used in general on any deteriorated articular surface including, for example, a deteriorated knee. It should be noted that the present invention is particularly useful when impact forces are required to be absorbed to assure long life of the implant.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A prosthesis comprising:
    a prosthetic element having a surface; and
    a hydrated polymethylmethacrylate 2-hydroxyethyl methacrylate copolymer film having an amount of 2-hydroxethyl methacrylate effective to improve elongation and having a first and second side, the first side disposed on at least a portion of the surface of the prosthetic element, the second side forming a bonding surface.
2. The prosthesis of claim 1, wherein
    the bonding surface is adapted to be fixedly attached to a bone by a bone cement.
3. The prosthesis of claim 1, wherein
    the prosthetic element surface is treated to prevent formation of a weak boundary layer upon bonding of the copolymer film to the prosthetic element surface.
4. The prosthesis of claim 3, wherein
    the prosthetic elemednt comprises metal.
5. The prosthesis of claim 4, wherein
    the treatment to prevent the formation of a weak boundary layer comprises degreasing the metal prosthetic element and thereafter acid etching the prosthetic element.
6. The prosthesis of claim 3, wherein
    the prosthetic element comprises a cobalt-chromium-molybdenum alloy, stainless steel, or titanium alloy.
7. The prosthesis of claim 5, wherein
    wherein the acid-etched prosthetic element surface is desmutted and passivated by treating the prosthetic element surface with an aqueous solution of hydrofluoric acid and nitric acid.
8. The prosthesis of claim 3, wherein
    the prosthetic element comprises ultra high molecular weight polyethylene.
9. The prosthesis of claim 8, wherein
    preventing the formation of a weak boundary layer comprises oxidizing the surface of the prosthetic element.
10. The prosthesis of claim 3, wherein
    the hydrated application of the polymethylmethacrylate 2-hydroxyethyl methacrylate copolymer film to the treated surface comprises providing a solution of hydrated polymethylmethacrylate 2-hydroxyethyl methacrylate and applying the solution to the treated surface.
11. The prosthesis of claim 2, wherein
    the prosthesis is a bone implant.
12. The prosthesis of claim 2, wherein
    the prosthesis being adapted to be fixedly attached to an articular surface of a bone.
13. The prosthesis of claim 12, wherein
    the articular surface of the bone comprises the ball portion of a ball and socket joint.
14. The prosthesis of claim 2, wherein
    the hydrated polymethylmethacrylate 2-hydroxyethyl methacrylate copolymer film has a thickness greater than about 0.0001 inch.
15. The prosthesis of claim 2, wherein
    the prosthesis is fixedly adhered to a bone by bone cement comprising hydrated polymethylmethacrylate 2-hydroxyethyl methacrylate copolymer.
16. A prosthesis comprising:
    a prosthetic element having surface; and
    a hydrated methylmethacrylate 2-hydroxyethyl methacrylate copolymer film having an amount of 2-hydroxethyl methacrylate effective to improve elongation and having a first and second side, the first side disposed on a least a portion of the surface of the prosthetic element, the second side forming a bonding surface, wherein the bonding surface is adapted to be fixedly attached to a bone by a bone cement comprising a hydrated polymethylmethacrylate 2-hydroxyethyl methacrylate copolymer.
17. The prosthesis of claim 16, wherein:
    the prosthetic element surface is treated to prevent formation of a weak boundary layer upon bonding of the copolymer film to the prosthetic element surface.
18. The prosthesis of claim 17, wherein
    the prosthetic element comprises metal.
19. The prosthesis of claim 18, wherein
    the treatment to prevent the formation of a weak boundary layer comprises degreasing the metal prosthetic element with an alkaline reagent and thereafter acid etching the prosthetic element.
20. The prosthesis of claim 17, wherein
    the metal prosthetic element comprises a cobalt-chromium-molybdenum alloy, stainless steel, or a titanium alloy.

21. The prosthesis of claim 19, wherein the acid-etched prosthetic element surface is desmutted and passivated by treating the prosthetic element surface with an aqueous solution of hyrdofluoric acid and nitric acid.

22. The prosthesis of claim 17, wherein the prosthetic element comprises ultra high molecular weight polyethylene.

23. The prosthesis of claim 22, wherein the treatment to prevent the formation of a weak boundary layer comprises oxidizing the surface of the prosthetic element.

24. The prosthesis of claim 17, wherein the application of the polymethylmethacrylate 2-hydroxyethyl methacrylate copolymer film to the treated surface comprises providing a solution of hydrated polymethylmethacrylate 2-hydroxyethyl methacrylate and applying the solution to the treated surface.

25. The prosthesis of claim 16, wherein the prosthesis is a bone implant.

26. The prosthesis of claim 16, wherein the prosthesis being adapted to be fixedly attached to an articular surface of a bone.

27. The prosthesis of claim 26, wherein the articular surface of the bone comprises the ball portion of a ball and socket joint.

28. The prosthesis of claim 16, wherein the hydrated polymethylmethacrylate 2-hydroxyethyl methacrylate copolymer film has a thickness greater than about 0.0001 inch.

29. The bone cement for use in fixedly adhering a prosthesis to a bone comprising:
a hydrated copolymer of polymethymethacrylate 2-hydroxyethyl methacrylate.

30. The bone cement of claim 29, wherein the prosthesis comprises a prosthetic element having a surface, the surface being adapted to be fixedly attached to the bone by the polymethylmethacrylate 2-hydroxyethyl methacrylate copolymer bone cement.

31. The prosthesis of claim 30, wherein the prosthesis is a bone implant.

32. The prosthesis of claim 30, wherein the prosthesis being adapted to be fixedly attached to an articular surface of a bone.

33. The prosthesis of claim 32, wherein the articular surface of the bone comprises the ball portion of a ball and socket joint.

34. A process for preparing an improved prosthesis comprising a prosthetic element having a surface, the prosthesis adapted to be joined to bone by a bone cement which comprises:
treating the prosthetic element surface to prevent formation of a weak boundary layer upon bonding of the bond cement to an applied film;
applying a polymethylmethacrylate 2-hydroxyethyl methacrylate copolymer film having an amount of 2-hydroxethyl methacrylate effective to improve elongation to the treated surface;
annealing the polymethylmethacrylate 2-hydroxyethyl methacrylate copolymer film; and
hydrating the polymethylmethacrylate 2-hydroxethyl methacrylate copolymer film to form a hydrated polymethylmethacrylate 2-hydroxyethyl methacrylate copolymer film.

35. A process in accordance with claim 34, wherein the prosthetic element comprises metal.

36. A process in accordance with claim 35, wherein the treatment to prevent formation of a weak boundary layer upon bonding of the bonding cement to an applied film comprises degreasing the metal prosthetic element with an alkaline reagent and thereafter acid etching the prosthetic element.

37. A process in accordance with claim 35, wherein the metal prosthetic element comprises a cobalt-chromium-molybdenum alloy, a titanium alloy, or stainless steel.

38. A process in accordance with claim 36, wherein wherein the prosthetic element surface is desmutted and passivated by treating the prosthetic element with an aqueous solution of hydrofluoric acid and nitric acid.

39. A process in accordance with claim 34, wherein the prosthetic element is composed of ultra high molecular weight polyethylene.

40. A process in accordance with claim 39, wherein the treatment to prevent the formation of a weak boundary layer upon bonding of the bone cement and an applied film comprises oxidizing the surface of the prosthetic element.

41. The process of claim 34, wherein the prosthesis is a bone implant.

42. The process of claim 34, wherein the prosthesis being adapted to be fixedly attached to an articular surface of a bone.

43. The process of claim 42, wherein the articular surface of the bone comprises the ball portion of a ball and socket joint.

44. The process of claim 34, wherein the hydrated polymethylmethacrylate 2-hydroxyethyl methacrylate copolymer film has a thickness greater than about 0.0001 inch.

45. The process of claim 34 wherein the film is hydrated by exposing the annealed film to an aqueous solution.

46. The process of claim 45 wherein said aqueous solution is a saline solution.

47. The process of claim 45 wherein said exposing is by packaging the prosthesis in said aqueous solution.

* * * * *

UNITED STATES PATENT AND TRADEMARK OFFICE
CERTIFICATE OF CORRECTION

PATENT NO. : 6,136,038
DATED : October 24, 2000
INVENTOR(S) : Simon Raab

It is certified that error appears in the above-identified patent and that said Letters Patent is hereby corrected as shown below:

<u>Column 4,</u>
Line 58, after "instance," delete "in" and insert therefor -- an --

<u>Column 11,</u>
Line 63, after "prosthetic" delete "elemednt" and insert therefor -- element --

<u>Column 12,</u>
Line 4, after "5," delete "wherein" and insert therefor -- further comprising: --
Line 43, after "on" delete "a" and insert therefor -- at --

<u>Column 13,</u>
Line 14, after "the" (second occurrence) insert -- hydrated --
Line 32, after "29." delete "The" and insert therefor -- A --

<u>Column 14,</u>
Line 43, after "process" delete "of" and insert therfor -- in accordance with --

Signed and Sealed this

Twenty-seventh Day of July, 2004

JON W. DUDAS
*Acting Director of the United States Patent and Trademark Office*